United States Patent
Kimura et al.

(10) Patent No.: US 7,668,408 B2
(45) Date of Patent: Feb. 23, 2010

(54) SUPPORT APPARATUS FOR OPTICAL CHARACTERISTIC MEASUREMENT, AND PROGRAM PRODUCT USED FOR SAME

(75) Inventors: Naoki Kimura, Sakai (JP); Toru Kobayashi, Ibaraki (JP); Norio Ishikawa, Osaka (JP)

(73) Assignee: Konica Minolta Sensing, Inc., Sakai-shi (JP)

( * ) Notice: Subject to any disclaimer, the term of this patent is extended or adjusted under 35 U.S.C. 154(b) by 736 days.

(21) Appl. No.: 11/398,792

(22) Filed: Apr. 6, 2006

(65) Prior Publication Data
US 2006/0229838 A1 Oct. 12, 2006

(30) Foreign Application Priority Data
Apr. 11, 2005 (JP) ............................. 2005-113353

(51) Int. Cl.
*G06K 7/10* (2006.01)
*G06K 9/20* (2006.01)
(52) U.S. Cl. ..................................... 382/321
(58) Field of Classification Search ................. 356/138, 356/496; 382/106–108, 199, 206, 286, 321
See application file for complete search history.

(56) References Cited

U.S. PATENT DOCUMENTS

| | | | | |
|---|---|---|---|---|
| 5,619,587 A | * | 4/1997 | Willoughby et al. | 382/141 |
| 5,796,868 A | * | 8/1998 | Dutta-Choudhury | 382/199 |
| 6,388,674 B1 | * | 5/2002 | Ito et al. | 345/590 |
| 7,009,640 B1 | * | 3/2006 | Ishii et al. | 348/223.1 |
| 7,268,887 B2 | * | 9/2007 | Kulawiec et al. | 356/496 |
| 2002/0118210 A1 | | 8/2002 | Yuasa et al. | |

FOREIGN PATENT DOCUMENTS

JP 06-078830 (U) 11/1994

* cited by examiner

*Primary Examiner*—Bhavesh M Mehta
*Assistant Examiner*—Gregory F Cunningham
(74) *Attorney, Agent, or Firm*—Sidley Austin LLP

(57) ABSTRACT

A support apparatus for optical characteristic measurement includes a measurement data inputter configured to input measurement data obtained by an optical characteristic measuring instrument, an image inputter configured to input an image of a measurement object, a measurement table in which the measurement data and the image of the measurement object corresponding to the measurement data are recorded, and a measurement data manager configured to record the measurement data inputted by the measurement data inputter in the measurement table so as to be associated with the image of the measurement object every time an optical characteristic of the measurement object is measured.

18 Claims, 10 Drawing Sheets

Fig.3

TB  Measurement Table

| object code (CB) | image code (CF) | measurement part number (CU) | measurement data number (CD) | measurement data (DS) |
|---|---|---|---|---|
| ABC1234 | 0001 | 01 | 01 | a*=··· |
| | | | 02 | a*=··· |
| | | | 03 | a*=··· |
| | | 02 | 01 | a*=··· |
| | | | 02 | a*=··· |
| | | 03 | 01 | a*=··· |
| ABC5678 | 0002 | 01 | 01 | a*=··· |
| | | | 02 | a*=··· |
| | | 02 | 01 | a*=··· |
| | | | 02 | a*=··· |
| | | | 03 | a*=··· |
| ABC5679 | 0003 | 01 | 01 | a*=··· |
| | | 02 | 01 | a*=··· |
| DEF1234 | 0004 | 01 | 01 | a*=··· |

SUPPORT APPARATUS FOR OPTICAL CHARACTERISTIC MEASUREMENT, AND PROGRAM PRODUCT USED FOR SAME

CROSS-REFERENCE TO RELATED APPLICATION

This application is based on Japanese Patent Application No. 2005-113353 filed in Japan on Apr. 11, 2005, the entire of which is hereby incorporated by reference.

BACKGROUND OF THE INVENTION

1. Field of the Invention

The present invention relates to a support apparatus for optical characteristic measurement by colorimeters, glossmeters, reflectance measuring instruments, transmittance measuring instruments, and other optical characteristic measuring instruments.

2. Description of the Related Art

In recent years, the importance of the color conditioning of products has been recognized in the fields of coating, molding, printing, textiles and the like. For this reason, in factories and the like, optical characteristic measurement such as color measurement by a colorimeter or gloss measurement by a glossmeter is frequently performed on objects of measurement such as products and parts.

Conventionally, an image of the measurement object has been used to manage the measurement data obtained by an optical characteristic measuring instrument. That is, the measurement value and the image data of the measurement object are separately captured into the computer, and the operator associates them with each other. It has also been proposed to attach a camera to a radiation thermometer takes an image of a measurement object by the camera simultaneously with the measurement, and superimpose the measurement value on the image of the measurement object taken by the camera when the image is printed. Thereby, the image and the measurement value are associated with each other.

It has also conventionally been proposed to associate the color value data obtained by measuring the color of the image displayed on the display with the position data in the image data in order that the color intended by the creator of the image information can be reproduced when the transmitted image information is reproduced on the receiver side.

However, according to the conventional method in which the measurement value and the image data of the measurement object are associated with each other by the operator, it is not always assured that the measurement value is that of the measurement object represented by the image data, and there is a possibility that the image data is associated with an irrelevant measurement value due to a simple mistake by the operator.

According to the method in which the measurement value is superimposed on the image of the measurement object taken by the camera when the image is printed, since the measurement value is superimposed on the image data, the measurement value cannot be used as it is. To use the measurement value, it is necessary to read the measurement value from the image data and re-input the measurement data by hand, and an input error can occur in that occasion.

According to the method in which the color value data obtained by measuring the color of the image displayed on the display is associated with the position data in the image data, the image data of the measurement object and the measurement value of the measurement object itself are not associated with each other. That is, not the measurement value of the measurement object itself but merely the measurement value of the image data of the measurement object shown on the display or the like is associated with the image data.

In addition, while the measurement object and the measurement part are specified by a language according to the conventional methods, with the specification by a language, there is a possibility that the operator mistakes the measurement object or measurement part when actually performing the measurement.

SUMMARY OF THE INVENTION

A principal object of the present invention is to provide a support apparatus for optical characteristic measurement capable of correctly associating the measurement object and the measurement data thereof with each other in the optical characteristic measurement, and a program product used for same.

Another object of the present invention is to provide a support apparatus for optical characteristic measurement capable of specifying the measurement object by an image, and a program product used for same.

The above-mentioned objects of the present invention are attained by providing a support apparatus for optical characteristic measurement comprising:

a measurement data inputter configured to input measurement data obtained by an optical characteristic measuring instrument;

an image inputter configured to input an image of a measurement object;

a measurement table in which the measurement data and the image of the measurement object corresponding to the measurement data are recorded; and a measurement data manager configured to record the measurement data inputted by the measurement data inputter in the measurement table so as to be associated with the image of the measurement object every time an optical characteristic of the measurement object is measured.

The above-mentioned objects of the present invention are also attained by providing a support apparatus for optical characteristic measurement comprising:

a measurement data inputter configured to input measurement data obtained-by an optical characteristic measuring instrument;

an image inputter configured to input an image of a measurement object;

an image registerer configured to register the inputted image of the measurement object;

an image selector configured to select an image corresponding to one measurement object from images registered by said image registerer;

a mode setter configured to set a normal mode or an image specification mode; and a measurement data manager that records, in the measurement table, the measurement data inputted by the measurement data inputter so as to be associated with the image of the measurement object every time an optical characteristic of the measurement object is measured, the measurement data manager recording, in the measurement table, the measurement data concerning the measurement object corresponding to the image inputted by the image inputter when the normal mode is set, the measurement data manager recording, in the measurement table, the measurement data concerning the measurement object corresponding to the image selected by the image selector when the image specification mode is set.

These and other objects, advantages and features of the invention will become apparent from the following description thereof taken in conjunction with the accompanying drawings, which illustrate specific embodiments of the invention.

BRIEF DESCRIPTION OF DRAWINGS

These and other objects, advantages and features of the invention will become apparent from the following description thereof taken in conjunction with the accompanying drawings in which:

FIG. 3 is a view showing an example of a measurement table;

DESCRIPTION OF THE PREFERRED EMBODIMENTS

Figure 1:
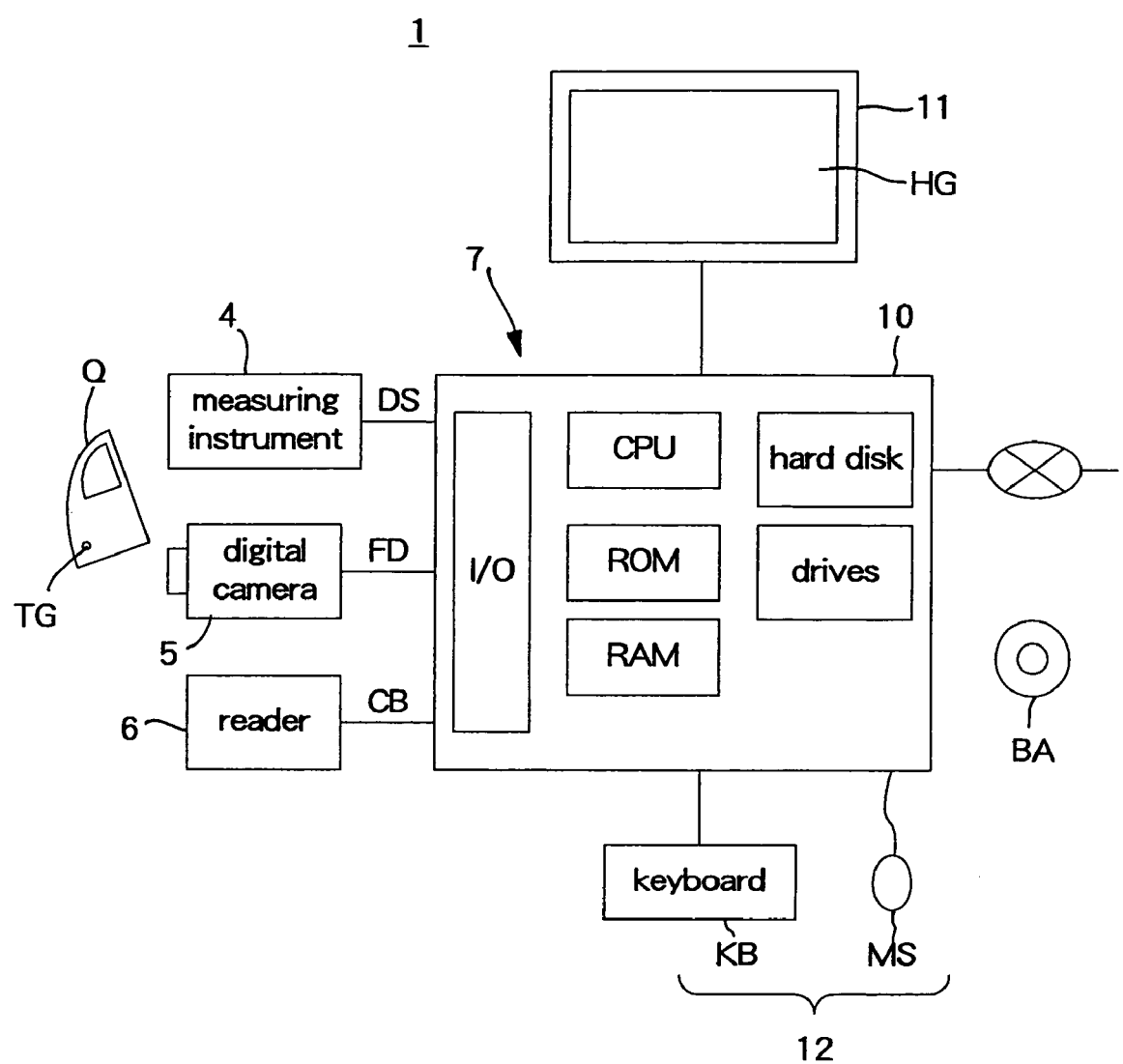
FIG. 1 is a block diagram showing the structure of an optical characteristic measuring instrument according to an embodiment of the present invention.
Figure 2:
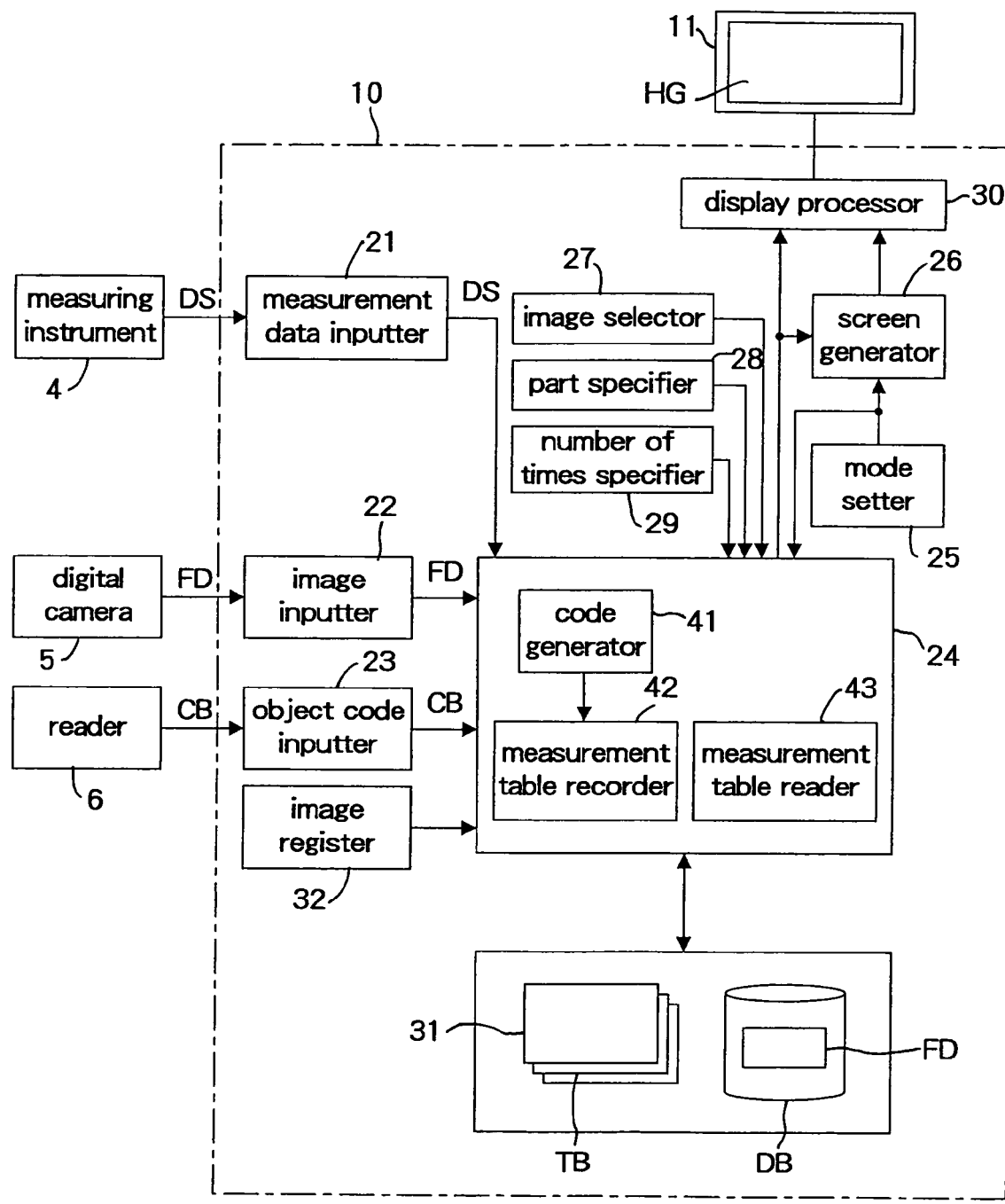
FIG. 2 is a block diagram showing the functional structure of an optical characteristic measurement support apparatus.

FIG. 1 is a block diagram showing the structure of an optical characteristic measuring system 1 according to an embodiment of the present invention. FIG. 2 is a block diagram showing the functional structure of an optical characteristic measurement support apparatus 7. FIG. 3 is a view showing an example of a measurement table TB.

In FIG. 1, the optical characteristic measuring system 1 includes a measuring instrument 4, a digital camera 5, a reader 6, and the optical characteristic measurement support apparatus 7.

As the measurement object Q, any object whose optical characteristic is measured is applicable. The present embodiment shows an example in which one of the measurement objects Q is a rear door which is a part of a car. The optical characteristic measuring system 1 measures the optical characteristic of various parts of the measurement object Q, and records and manages the obtained measurement data by the optical characteristic measurement support apparatus 7.

The measuring instrument 4 is an instrument, such as a colorimeter, a glossmeter, a reflectance measuring instrument or a transmittance measuring instrument, that measures the optical characteristic of the measurement object Q. The measuring instrument 4 is connected to the optical characteristic measurement support apparatus 7 by a cable or by radio, and outputs measurement data DS to the optical characteristic measurement support apparatus 7. The measuring instrument 4 is also capable of receiving instruction data such as a measurement start instruction from the optical characteristic measurement support apparatus 7 and controlling the operation in response to an instruction from the optical characteristic measurement support apparatus 7. Additionally, the measuring instrument 4 transmits and receives various pieces of data and signals to and from the optical characteristic measurement support apparatus 7.

The digital camera 5 captures an image of the measurement object Q to obtain its image FD. As the digital camera 5, both one that takes still images and one that takes moving images are applicable. The digital camera 5 may be provided separately from the measuring instrument 4, or may be provided integrally with the measuring instrument 4. In particular, when the measuring instrument 4 has a configuration that is manually held by the user (measurer) to view the measurement object Q like a luminance meter, there is a significant advantage in integrally combining the digital camera 5 with the measuring instrument 4.

Instead of the digital camera 5, one that captures the image FD of the measurement object Q, or an interface therefor may be provided.

The reader 6 reads the object information embedded in the measurement object Q, and outputs an object code CB. When an electronic memory such as an IC tag TG is embedded in the measurement object Q, the reader 6 communicates with the IC tag TG, reads the object code CB recorded on the IC tag TG, and outputs it. When a bar code is added to the measurement object Q, the reader 6 reads the bar code, and outputs the object code CB. The reader 6 may be provided separately from the measuring instrument 4, or may be provided integrally with the measuring instrument 4.

The optical characteristic measurement support apparatus 7, which supports the measurement by the measuring instrument 4, records the obtained measurement data DS in a measurement table together with an image of the measurement object Q and manages them. The optical characteristic measurement support apparatus 7 includes a processor 10, a display 11, and input devices such as a keyboard KB and a mouse MS.

The processor 10 is provided with a CPU, memories such as a ROM and a RAM, a hard disk, various drives, a communication interface, various peripheral circuits, and a control circuit. In the hard disk, various files and databases are stored. The databases are transferred and copied between the hard disk and the memories. Moreover, in the hard disk, a support software program for the optical characteristic measurement and software programs for the optical measurement and optical characteristic management of the measurement object Q are installed. These software programs are read in a memory as required, and executed by the CPU. In the memories, various parameters, arithmetic expressions and the like are stored as required. Moreover, connection is made to an external network through a network interface so that various programs and data can be transmitted and received. Moreover, a media drive is provided so that recording media BA such as a flexible disk, a CD-ROM, a magneto-optical disk, a memory chip and a memory card can be accessed. The program according to the present invention can be stored in these recording media BA. Therefore, the computer program according to the present invention can be provided in a condition of being recorded on the recording media BA or being downloaded through a network.

The keyboard KB and the mouse MS are used for the user to provide various instructions and commands and input data on screens displayed on a display surface HG of the display 11, and are also used for the user to input various pieces of data and provide commands to the processor 10. On the display surface HG of the display 11, various screens described later, various pieces of data, characters and images are displayed.

As shown in FIG. 2, the processor 10 is provided with a measurement data inputter 21, an image inputter 22, an object code inputter (an object discrimination information inputter) 23, a measurement data manager 24, a mode setter 25, a screen generator 26, an image selector 27, a part specifier 28, a number of times specifier 29, a display processor 30, a storage unit 31, and an image registerer 32. The measurement data manager 24 is provided with a code generator 41, a measurement table recorder 42, and a measurement table reader 43. In the storage unit 31, the measurement table TB and an image database DB are stored.

The measurement data inputter 21 inputs every measurement the measurement data DS measured by the measuring instrument 4. Examples of the measurement data DS include the color value, the gloss value, the reflectance, the transmittance, the measurement time, and the measurement condition.

The image inputter 22 inputs the image FD of the measurement object Q from the digital camera 5 or other image taking means or image storing means. The image FD includes an image of the measurement parts of the measurement object Q. Therefore, when the measurement parts are not present on the same plane, a plurality of images FD are inputted for one measurement object Q. Even when the measurement parts are present on the same plane, there are cases where a plurality of images FD are inputted for clearly showing the measurement parts. The image FD may be part of the measurement object Q. Moreover, the image FD may be one obtained by taking the same part at different angles.

The inputted image FD is stored in the image database DB of the storage unit 31 together with an image code CF. When a plurality of images FD are inputted, the image code CF is assigned to each image FD for identification, and the images FD are associated with one another by the image code CF. In actuality, the image FD is present as image data.

The object code inputter 23 inputs the object code CB read by the reader 6 from the measurement object Q. When no object information is attached to the measurement object Q, the user can input the object code CB by operating the keyboard KB.

The measurement data manager 24 records the inputted measurement data DS in the measurement table TB so as to be associated with the image FD, a measurement part number CU and a measurement data number CD every time the optical characteristic is measured by the measuring instrument 4 for the measurement object Q corresponding to the image FD inputted from the measurement data inputter 21. The measurement data manager 24 registers the inputted image FD in the measurement table TB or the image database DB together with the image code CF on an instruction of the image registerer 32.

The code generator 41 assigns the image code CF to the inputted image FD, assigns the measurement part number CU to the specified measurement part, and assigns the measurement data number CD to the measurement data DS of each time of the specified number of times of measurement.

The measurement table recorder 42 records the object code CB, the image code CF, the measurement part number CU, the measurement data number CD, and the measurement data DS in the measurement table TB. The measurement table recorder 42 also records information representative of whether the measurement table TB is one for a normal mode or one for a TASK mode (image specification mode) in the measurement table TB. Moreover, the measurement table recorder 42 records link information indicating that the data recorded in the measurement table TB is associated with other data. The measurement table recorder 42 records other necessary data in the measurement table TB.

The measurement table reader 43 reads out necessary data from the measurement table TB. For example, it reads out the image FD selected by the image selector 27 or the data corresponding thereto.

The mode setter 25 sets the normal mode or the TASK mode (image specification mode). When the normal mode is set, the measurement data manager 24 records into the measurement table TB the measurement data DS concerning the measurement object Q corresponding to the inputted image FD, and when the TASK mode is set, the measurement data manager 24 records into the measurement table TB the measurement data DS concerning the measurement object Q corresponding to the image FD selected by the image selector 27. The setting and the selection of these mode can be performed by the user operating the keyboard KB or the mouse MS on a selection screen displayed on the display surface HG.

The screen generator 26 generates various screens displayed on the display surface HG of the display 11. Moreover, the screen generator 26 stores a pre-generated screen and outputs it to the display processor 30 in response to an instruction. For example, the screen generator 26 generates an image input screen HG1 to prompt the input of the image FD of the measurement object Q. The image input screen HG1 shows a message such as "Please input the image of the measurement object Q." or "Please make a selection from among the displayed images." When the normal mode is set, the image input screen HG1 is displayed on the display surface HG before the measurement data DS is inputted. This function of the image generator 26 corresponds to the input screen display means of the present invention.

The image selector 27 selects a necessary image FD from among the images FD recorded in the measurement table TB, from among the images FD stored in the image database DB, or from among the images FD displayed on the display surface HG in response to an instruction or the like. For example, the image selector 27 selects the image FD corresponding to one measurement object Q from the measurement table TB in response to the user's instruction. In this case, the user can make a selection from among the images FD displayed on the display surface HG to provide the instruction, or can specify the object code CB, the image code CF, the measurement part number CU, the measurement data number CD or the like to provide the instruction. In the case of the TASK mode, the image selector 27 selects the image FD from the predetermined measurement table TB for the TASK mode. The selected image FD is displayed on the display surface HG.

The part specifier 28 specifies a measurement part BS of the measurement object Q as required. To specify the measurement part BS, for example, the user specifies a necessary part with the mouse MS or the like while viewing the image FD displayed on the display surface HG.

The number of times specifier 29 specifies the number of times N the measurement is performed on the same part of the measurement object Q as required. When the number of times N is not specified, "1" is set as the default value.

The display processor 30 performs the processing to display various screens, images, messages, data and the like on the display surface HG of the display 11.

The image registerer 32 performs the processing to previously input the image FD of the measurement object Q for registration.

The measurement table TB is for recording the measurement data DS and the image FD of the measurement object Q corresponding to the measurement data DS so as to be associated with each other.

As shown in FIG. 3, the measurement table TB includes items such as the object code CB, the image code CF, the measurement part number CU, the measurement data number CD and the measurement data DS.

The object code CB is a management code or an identification code for managing the measurement object Q. The object code CB includes, for example, the name, the kind, the applied model, the color, the lot number, the date of manufacture, the place of manufacture and the serial number of the object as required.

The image code CF is an identification code for identifying the image FD of the measurement object Q. The measurement part number CU is a code (number) assigned to each part measured or to be measured by the measuring instrument 4 with respect to one measurement object Q identified by the image code CF. The measurement data number CD is a code (number) assigned to each piece of measurement data DS with respect to one part of measurement object Q identified by the measurement part number CU. The measurement data DS is data (measurement value) obtained by the measuring instrument 4 actually performing the measurement. There are cases where a plurality of pieces of measurement data DS are present for one measurement data number CD.

The block diagram shown in FIG. 2 shows an example of the functional structure of the optical characteristic measurement support apparatus 7, and various other structures that realize the function described in the present specification are adoptable.

Such an optical characteristic measurement support apparatus 7 can be realized, for example, by using a personal computer or a workstation.

Next, the method of measurement by the optical characteristic measuring system 1, the processing to record the measurement data DS and the processing to create the measurement table TB will be described with reference to the flowcharts.

Figure 4:
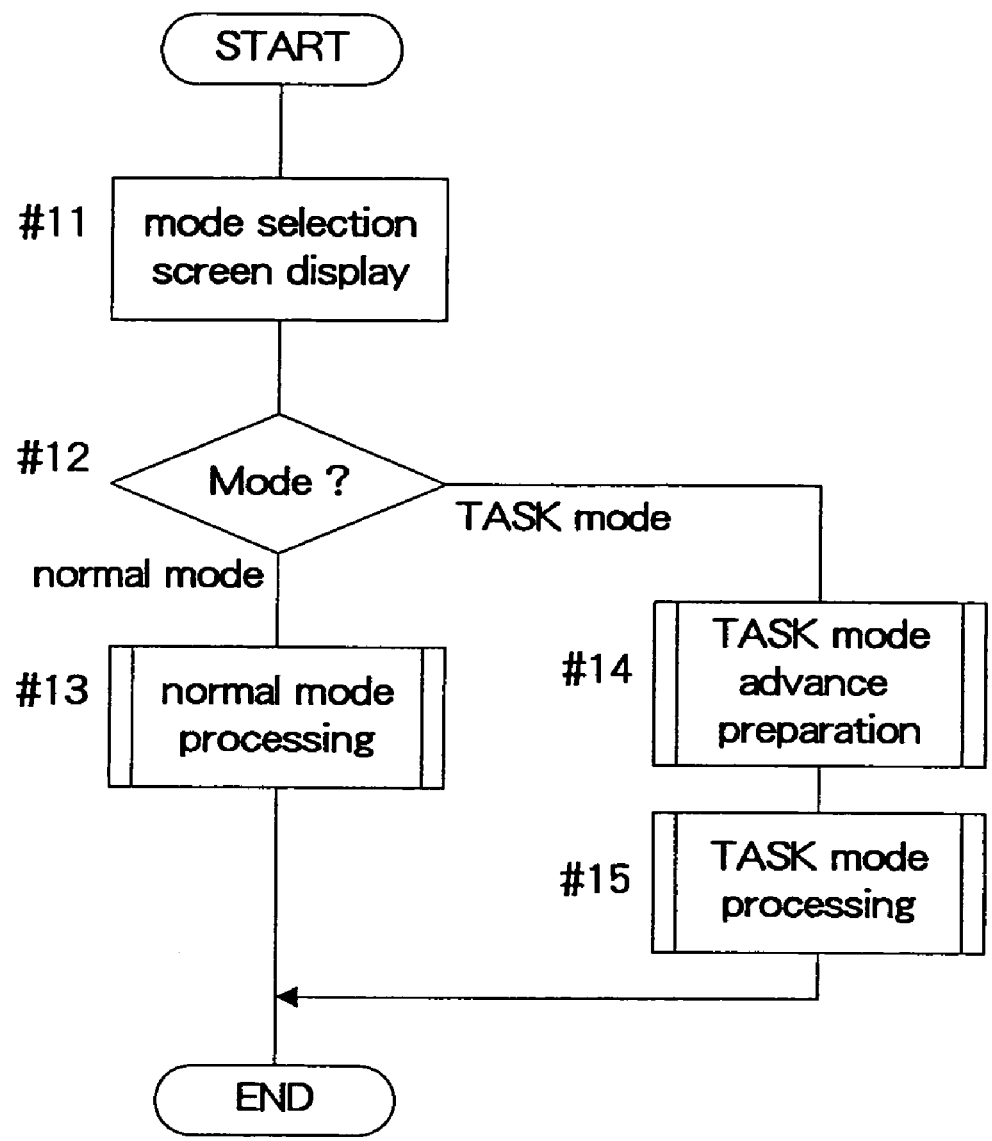
FIG. 4 is a main flowchart.
Figure 5:
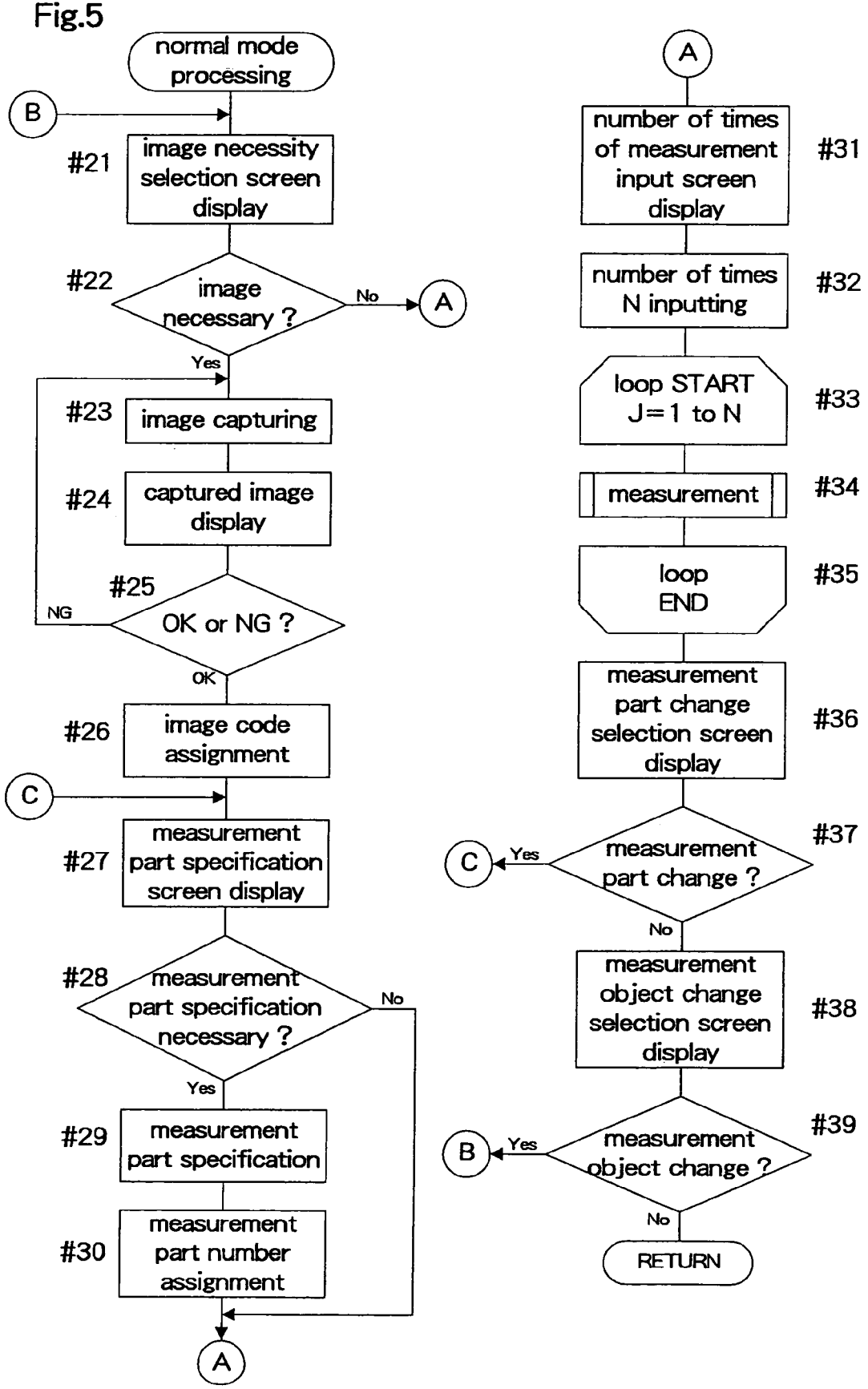
FIG. 5 is a flowchart showing a normal mode processing.
Figure 6:
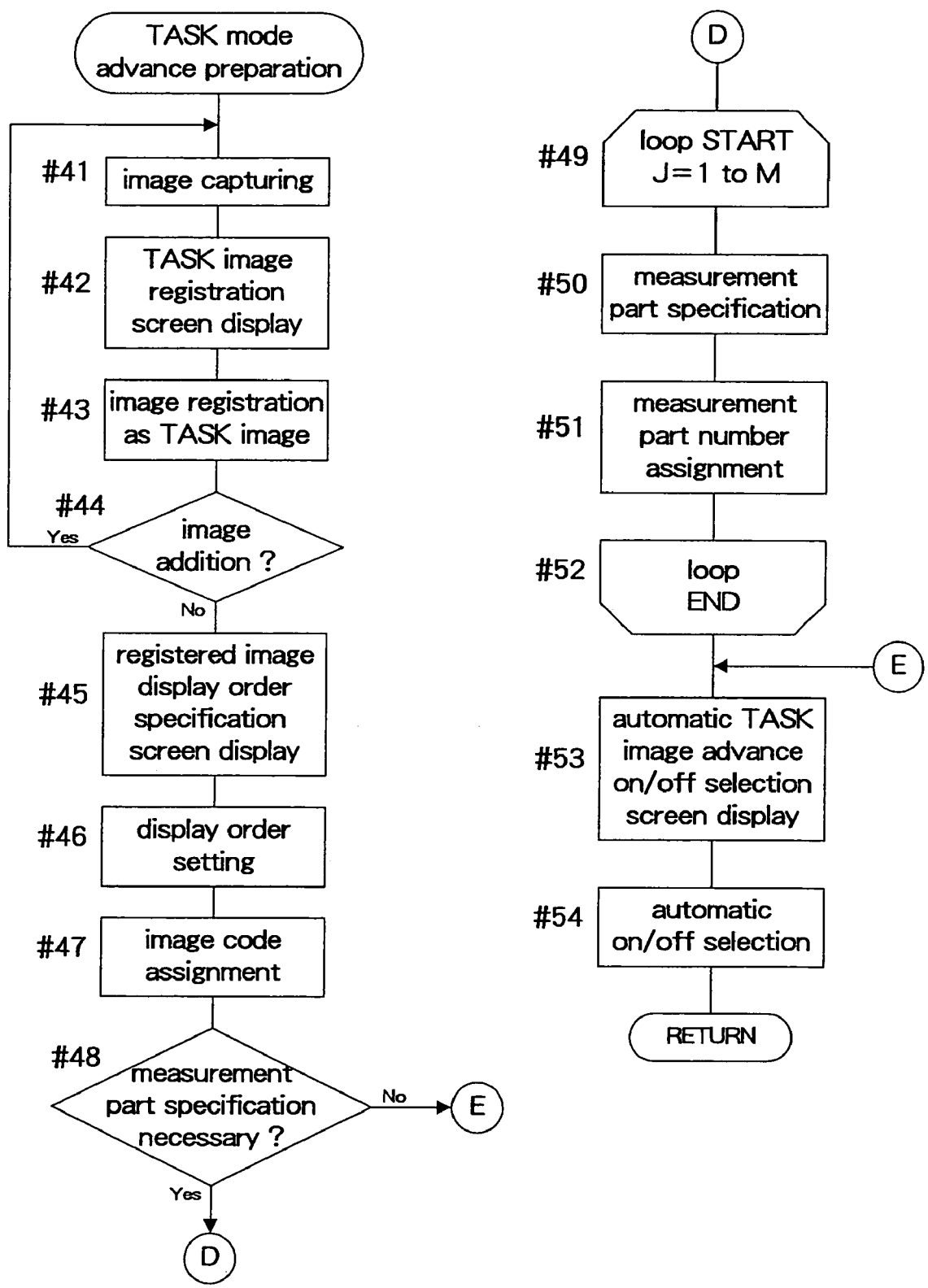
FIG. 6 is a flowchart showing a TASK mode advance preparation.
Figure 7:
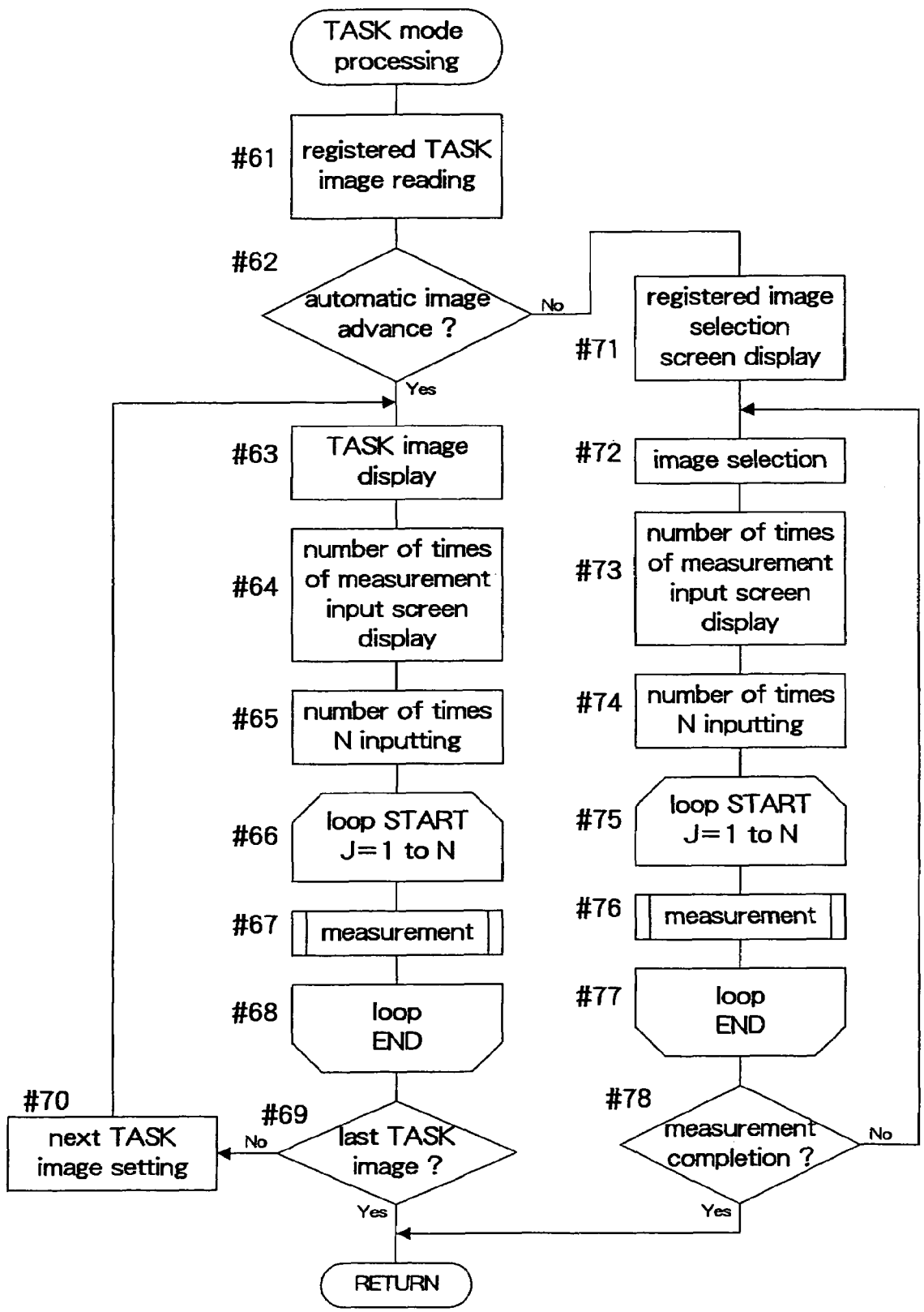
FIG. 7 is a flowchart showing a TASK mode processing.
Figure 8:
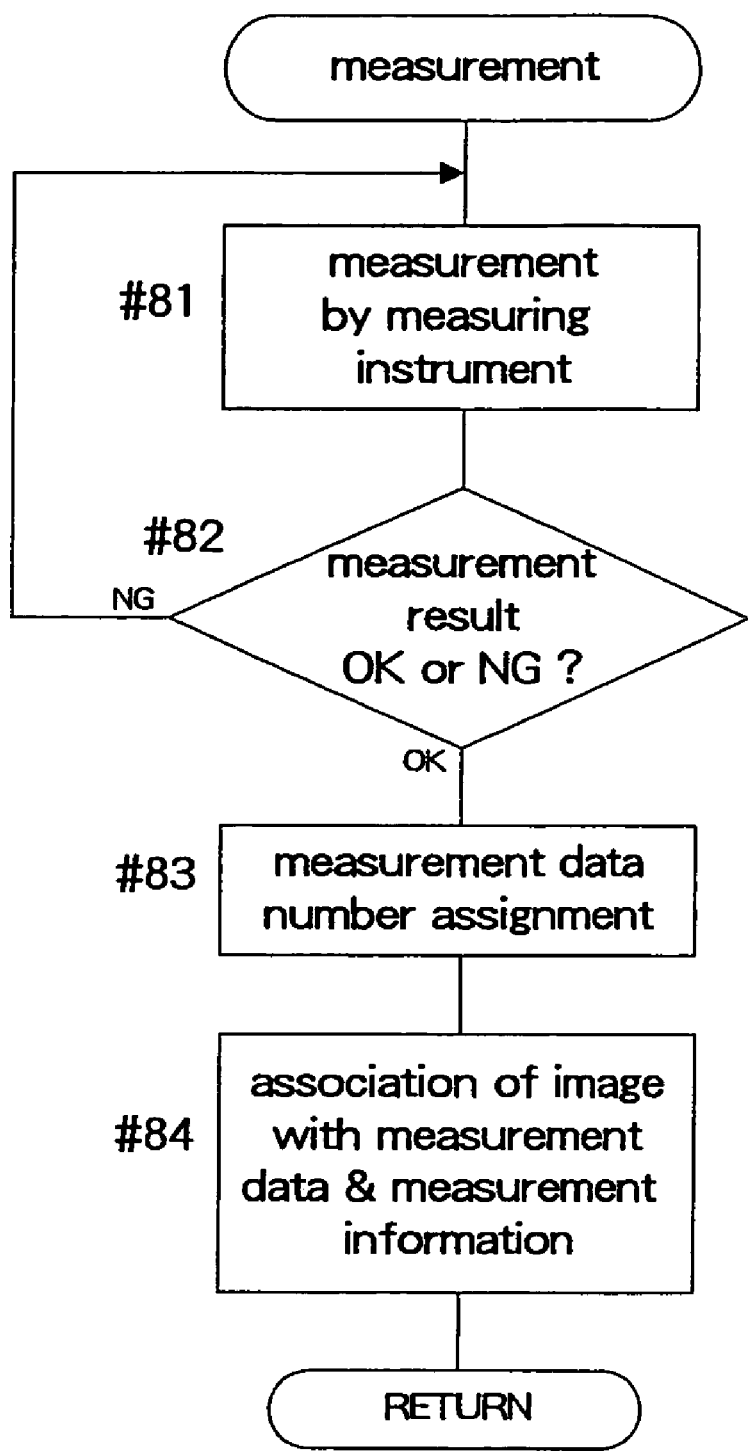
FIG. 8 is a flowchart showing the measurement processing.

FIG. 4 is a main flowchart. FIG. 5 is a flowchart showing the normal mode processing. FIG. 6 is a flowchart showing the TASK mode advance preparation. FIG. 7 is a flowchart showing the TASK mode processing. FIG. 8 is a flowchart showing the measurement processing.

In FIG. 4, first, the mode selection screen is displayed on the display surface HG of the display 11 (#11). The mode selection screen is for asking the user which of the normal mode and the TASK mode is set.

The TASK mode is a mode in which the images FD of the measurement object Q are registered in advance (advance preparation), the image FD selected from among the registered images FD is displayed on the display surface HG, and the user views the displayed image FD and performs the measurement by the measuring instrument 4 on the measurement object Q coinciding with the displayed image FD. The preregistered image FD is stored in an appropriate folder of the image database DB together with the image code CF, and the image code CF is recorded in the measurement table TB for the TASK mode. In the advance preparation, the measurement part and the number of times of measurement may be registered as well as the images FD. That is, the TASK mode is a mode in which a part of the part, other than the measurement data DS, of the measurement table TB is previously created. In the TASK mode, the contents of the previously created measurement table TB for the TASK mode are displayed on the display surface HG, and according to the displayed contents, the user performs the measurement by using the measurement table TB as the operation instruction.

When the mode selection screen is displayed, the user specifies the mode with the mouse MS or the like (#12). When the normal mode is specified, the normal mode processing is performed (#13). When the TASK mode is specified, the TASK mode advance preparation is performed (#14), and the TASK mode processing is performed (#15).

In FIG. 5, in the normal mode processing, an image necessity selection screen is displayed on the display surface HG (#21). The user selects whether the image FD is necessary or not (#22). Normally, the image FD is necessary. The image FD of the measurement object Q is taken by the digital camera 5 (#23). Instead of the image capturing by the digital camera 5, the image FD of the measurement object Q may be captured from the outside or the inside. The taken image FD is displayed as an image capturing result selection screen on the display surface HF (#24). Viewing the image FD on the image capturing result selection screen, the user determines whether the image FD is OK or not, and selects OK or NG (#25). When NG is selected, the process returns to step #23, and image capturing is performed again. When OK is selected, the image code CF is assigned to the image FD (#26).

Then, the image FD is displayed on the display surface HG as a measurement part specification screen (#27). On the measurement part specification screen, the user selects whether the measurement part specification is necessary or not (#28). When it is necessary, the user specifies the measurement part on the screen (#29). In the specification of the measurement part, for example, the user clicks on the part, to be specified as the measurement part, of the image FD displayed on the display surface HG with the mouse MS. The measurement part number CU is assigned to the specified measurement part (#30).

A number of times of measurement input screen is displayed on the display surface HG (#31). The user inputs the number of times N for the previously specified measurement part (#32). The processing from the loop START (#33) to the loop END (#35) is repeated the inputted number of times N. Consequently, the measurement processing is repeated N times (#34).

A measurement part change selection screen is displayed on the display surface HG (#36). On the measurement part change selection screen, the user specifies whether a measurement part is added or not (#37). When a change (addition) of the measurement part is specified, the process returns to step #27, and the measurement part specification screen is displayed. When the measurement part is not changed (added), a measurement object change selection screen is displayed (#38) On the measurement object change selection screen, the user specifies whether the measurement object Q is changed or not (#39). When a change of the measurement object Q is specified, the process returns to step #21, and the image necessity selection screen is displayed when the measurement object Q is not changed, the processing is ended, and the process returns to the previous routine.

Figure 10:
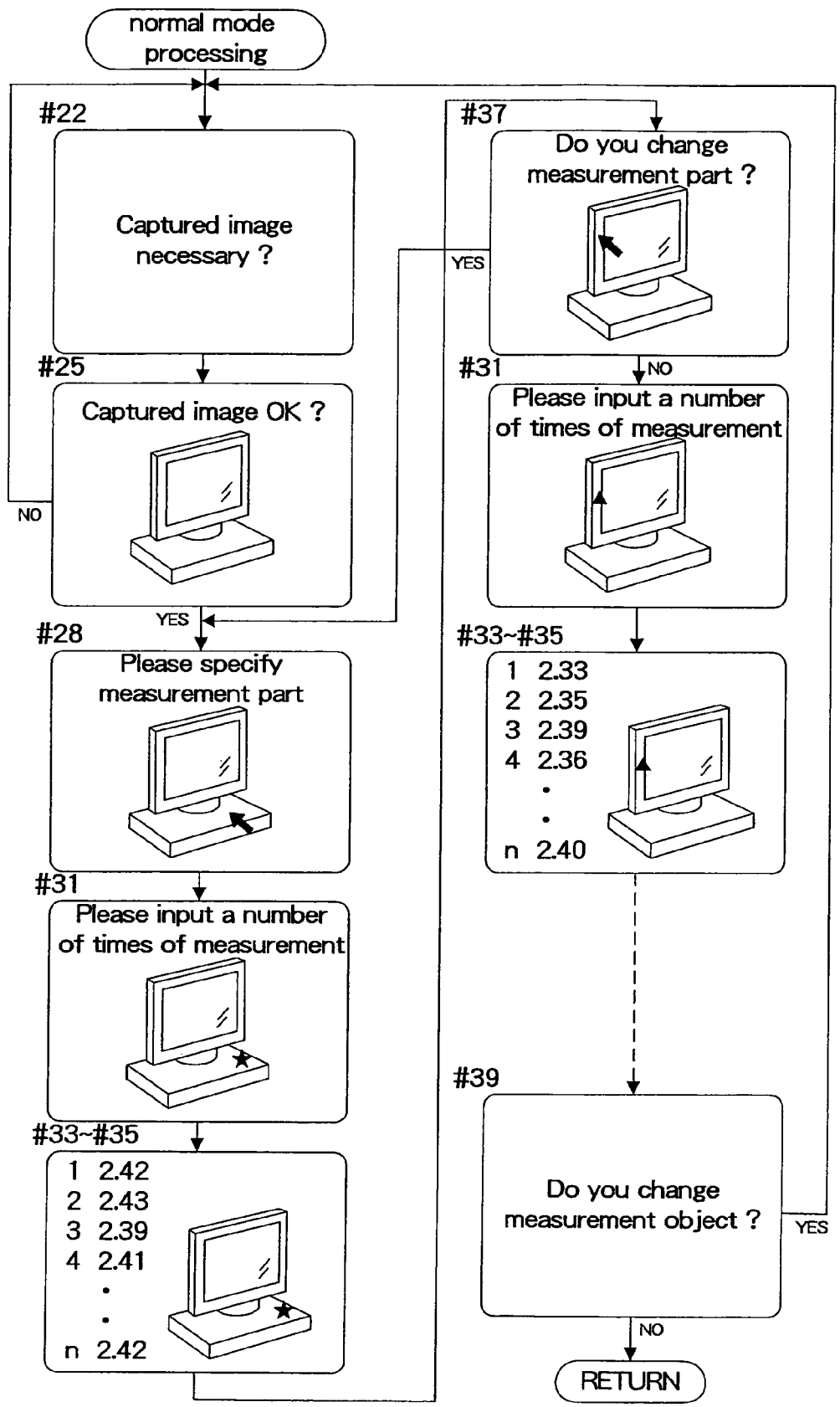
FIG. 10 shows examples of screens displayed on the display surface in the normal mode processing.

FIG. 10 shows examples of principal screens displayed on the display surface HG in the normal mode processing described above. The numerals #22 to #39 shown in FIG. 10 indicate that the screens correspond to steps #22 to #39 in FIG. 5.

In FIG. 6, in the TASK mode advance preparation, first, the image FD is captured (#41). A screen for registering the image FD used in the TASK mode (TASK image registration screen) is displayed (#42). The displayed image FD is registered in the image database DB as an image for TASK (#43). When another image FD is added (YES of #44), the process returns to step #41, and the image FD is captured. In this manner, a multiplicity of (M) images FD are registered. When a plurality of measurement objects Q are registered, these may be objects relevant to each other or may be objects irrelevant to each other.

When no image FD is added (No of #44), a registered image display order specification screen for specifying the order of display of the registered images FD is displayed (#45). On the registered image display order specification screen, the user sets the order of display (#46). The image code CF is assigned in accordance with the order of display (#47).

With respect to each image FD, whether the specification of the measurement part is necessary or not is selected (#48). When it is necessary, the processing from the loop START (#49) to the loop END (#52) is repeated a number of times equal to the number M of registered images FD. Consequently, the specification of the measurement part and the assignment of the measurement part number CU are performed-M times (#50, #51).

An automatic image advance on/off selection screen for selecting whether the automatic advance of the image FD for the TASK mode is performed or not is displayed (#53). The user selects on or off on the screen (#54). When the automatic image advance is on, a slide mode is set in the TASK mode processing performed later, and a plurality of images FD are automatically displayed in succession, whereby the measurement object Q to be measured is automatically specified.

By these processings, the measurement table TB for the TASK mode is created. In the measurement table TB for the TASK mode, that this table is for the TASK mode is recorded, and the measurement table TB is incomplete as the measurement table TB. Whether the automatic image advance is on or off selected by the user is also recorded in the measurement table TB for the TASK mode.

The operation of the TASK mode advance preparation may be performed by a user different from the user performing the measurement. For example, the manager who provides a measurement instruction in the TASK mode may be the user in the TASK mode advance preparation.

In FIG. 7, in the TASK mode processing, the images FD registered in the measurement table TB for the TASK mode is read in (#61). When the automatic image advance is on (#62), the process proceeds to step #63, and when it is off, the process proceeds to step #71. The on and off of the automatic image advance can be changed by the user on the screen. For example, even when the automatic image advance is on, when the measurement object Q corresponding to the displayed image FD does not show up, the user can switch off the automatic image advance to perform the measurement of another measurement object Q.

At step #63, the image FD for the TASK mode is displayed on the display surface HG. The number of times of measurement input screen is displayed on the display surface HG (#64). The user inputs the number of times N (#65).

That is, in the flowchart of the present embodiment, even in the TASK mode, the user (measurer) inputs the number of times N. However, the number of times N may be preset. In this case, the user performs the measurement the set number of times N.

The processing from the loop START (#66) to the loop END (#68) is repeated the inputted number of times N. Consequently, the measurement processing is repeated N times (#67). When there is still an image FD for the TASK mode (#69), the next image FD is set (#70), and the processing from step #63 is repeated.

When the automatic image advance is off at step #62, a registered image selection screen for selecting the image FD registered for the TASK mode (#71) is displayed. The user selects the image FD on the screen (#72). At this time, the user can select a link image associated with the image FD. By selecting a series of associated images FD and performing the measurement on a plurality of measurement objects Q or a plurality of measurement parts by the selected images, a link is established among the pieces of the measurement data DS, and the color difference and the like can be calculated by performing a calculation among the linked pieces of measurement data DS later.

The number of times of measurement input screen is displayed on the display surface HG (#73). The user inputs the number of times N (#74).

The processing from the loop START (#75) to the loop END (#77) are repeated by the number of times N, and the measurement processing is repeated by N times (#76). When the measurement is further performed (YES of #78), the process returns to step #72, and the image FD is selected.

In FIG. 8, in the measurement processing, the measurement by the measuring instrument 4 is performed until the result is OK (#81, #82). When the measurement data DS is OK, the measurement data number CD is assigned to the measurement data DS (#83). These measurement data DS and image FD as well as measurement part number CU and measurement data number CD (measurement information) are recorded in the measurement table TB so as to be associated with one another (#84).

Although the object code CB is not touched on in the description of the flowchart given above, it is necessary for the object code CB only to be inputted by the user from the keyboard KB or read from the measurement object Q by the reader 6 and be recorded in the measurement table TB. The object code CB is not necessarily recorded. For example, when the measurement object Q is a handmade item, there are cases where the measurement object Q can be identified only by the image FD without the assignment of the object code CB.

Next, a flowchart of a case where the object code CB of an IC tag TG embedded in the measurement object Q is read and recorded in the measurement table TB will be described.

Figure 9:
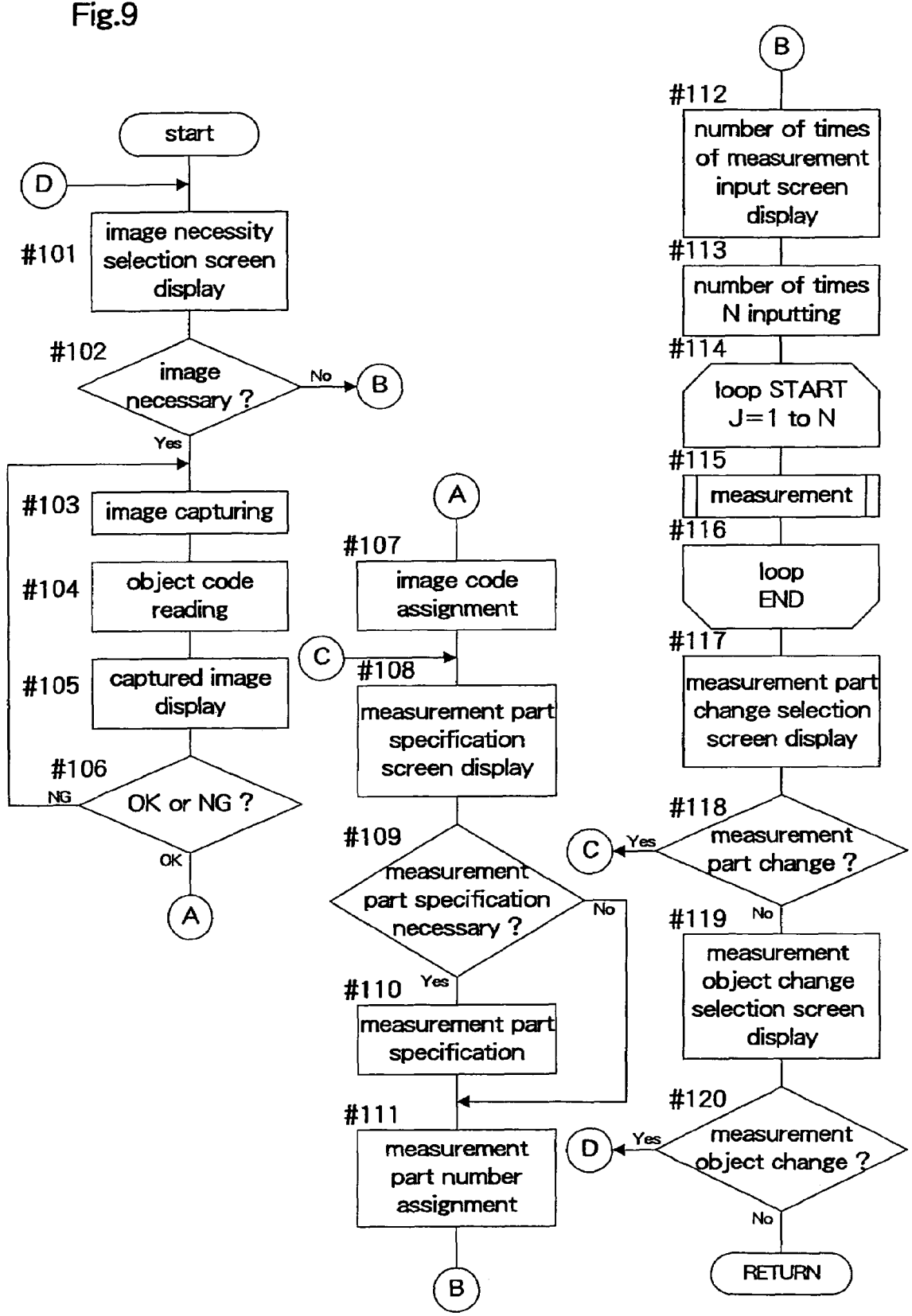
FIG. 9 is a flowchart showing the normal mode processing when an object code is read.

FIG. 9 is a flowchart showing the normal mode processing when the object code CB is read.

In FIG. 9, the image necessity selection screen is displayed on the display surface HG (#101). The user selects whether the image FD is necessary or not (#102). The image FD of the measurement object Q is taken by the digital camera 5 (#103). The object code CB is read by the reader 6 (#104). The taken image FD is displayed (#105). Viewing the image FD, the user selects OK or NG (#106). When it is OK, the image code CF is assigned to the image FD (#107). At this time, the object code CB may be recorded so as to be associated with the image FD. In any case, the object code CB is recorded in the measurement table TB so as to be associated with the measurement data DS.

The processing from step #108 will not be described because it is the same as the processing from step #27 to step #39 in FIG. 5.

At step #84 shown in FIG. 8, the measurement data DS and the image FD as well as the measurement part number CU, the measurement data number CD and the object code CB (measurement information) are recorded in the measurement table TB so as to be associated with one another.

According to the optical characteristic measuring system 1 of the embodiment described above, after the image FD of the measurement object Q to be measured is inputted or selected, the measurement is performed on the measurement object Q and the measurement data DS inputted from the measuring instrument 4 is recorded in the measurement table TB so as to be automatically associated with the image FD, the measurement object Q and the measurement data DS thereof can be correctly associated with each other.

In addition, the object code CB embedded in the measurement object Q is read by the reader 6 and recorded in the measurement table TB so as to be automatically associated with the measurement data DS, so that these can be correctly associated with each other. Further, with respect to the measurement part of the measurement object Q and the measurement data DS obtained by a plurality of number of times of measurement on the same measurement part, the image FD and the measurement data DS are recorded in the measurement table TB so as to be automatically associated with each other, so that these can be correctly associated with each other.

According to the measurement table TB of the embodiment described above, the object code CB, the image FD, the measurement part and the measurement data DS of the measurement object Q can be reliably associated with one another. Further, it is easy to search for data and re-sort data later.

Moreover, by establishing a link among a plurality of images FD, measurement parts or pieces of measurement data DS, the color difference among a plurality of measurement objects Q or measurement parts can be automatically calculated. By displaying the linked measurement object Q and measurement parts in the image FD, the parts between which the color difference is calculated can be visually recognized. For example, when an upper part and a lower part of a rear door are specified as the measurement parts, by displaying the images FD thereof, the color nonuniformity can be easily recognized. When a rear door and a bumper are specified as the measurement objects Q, the color difference therebetween can be easily recognized.

In the TASK mode, it can be performed to display the contents of the previously created measurement table TB for the TASK mode on the display surface HG and specify the measurement object Q by the image FD. Since the measurement is sequentially performed according to the displayed contents, the user can easily and precisely perform the measurement without mistaking the measurement object Q or the measurement part.

By recording information on the measurement object Q, the measurement condition, the cautions in performing the measurement and other comments together with the image FD of the measurement object Q and displaying them to the user in the TASK mode, a correct instruction can be provided to the user by the image. While these images are displayed on the display surface HG of the display 11, it may be performed to provide a display on the measuring instrument 4 and display the images on the display.

While in the flowchart of the above-described embodiment, the object code CB, the image code CF, the measurement part number CU and the measurement data number CD are recorded in the measurement table TB after the measurement is performed, instead of this, they may be recorded in the measurement table TB when they are assigned. It may be performed to previously record the code or the number in the measurement table TB and associate them with recording positions of the measurement table TB when the image FD and the measurement part are specified or the measurement data DS is inputted. As the method of recording the code and the number so as to be associated with the measurement data DS, various methods are adoptable.

While the image code CF is recorded in the measurement table TB in the above-described embodiment, instead of this, the image FD itself may be recorded in the measurement table TB. The format and the like of the measurement table TB can be changed variously. While in the TASK mode advance preparation, the image code CF of the inputted image FD is recorded in the measurement table TB that is usable in the normal mode although it is for the TASK mode, the table for the normal mode and the table for the TASK mode may be completely separate ones. That is, in the TASK mode advance preparation, the inputted image FD, the image code CF, the measurement part and the like are recorded in an exclusive measurement table, and in the TASK mode, they are read from the exclusive measurement table and recorded in the measurement table TB.

While the optical characteristic measurement support apparatus 7 and the measuring instrument 4 are separate in the above-described embodiment, they may be integrated by incorporating the function of the optical characteristic measurement support apparatus 7 into the measuring instrument 4. Moreover, the digital camera 5 or the like may be incorporated in the measuring instrument 4 as described above.

Although the present invention has been fully described by way of examples with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. An electronic support apparatus for optical characteristic measurement comprising:
   an electronic measurement data inputter configured to input optical characteristic measurement data obtained by an optical characteristic measuring instrument;
   an electronic image inputter configured to input an image of a measurement object;
   an electronically stored measurement table in which the optical characteristic measurement data and the image of the measurement object corresponding to the measurement data are recorded; and
   an electronic measurement data manager configured to record the optical characteristic measurement data inputted by the measurement data inputter in the measurement table so as to create an association with the image of the measurement object every time an optical characteristic of the measurement object is measured.

2. The electronic support apparatus as claimed in claim 1, further comprising:
   an electronic part specifier configured to specify a measurement part of the measurement object;
   wherein said measurement data manager assigns a measurement part number to the part specified by said part specifier, and records the inputted optical characteristic measurement data in the measurement table so as to create an association with the measurement part number.

3. The electronic support apparatus as claimed in claim 1, further comprising:
   an electronic number of times specifier configured to specify the number of times the optical characteristic measurement is performed on the same part of the measurement object;
   wherein said measurement data manager assigns a measurement data number to the optical characteristic measurement data of each time of the specified number of times of measurement, and records the inputted optical characteristic measurement data in the measurement table so as to create an association with the measurement data number.

4. The electronic support apparatus as claimed in claim 1, further comprising:
   an electronic object discrimination information inputter configured to input object discrimination information to discriminate the measurement object;
   wherein said measurement data manager records the inputted optical characteristic measurement data in the measurement table so as to create an association with the object discrimination information.

5. An electronic support apparatus for optical characteristic measurement comprising:
- an electronic measurement data inputter configured to input measurement data obtained by an optical characteristic measuring instrument;
- an electronic image inputter configured to input an image of a measurement object;
- an electronic image registerer configured to register the inputted image of the measurement object;
- an electronic image selector configured to select an image corresponding to one measurement object from images registered by said image registerer;
- an electronic mode setter configured to set a normal mode or an image specification mode; and
- an electronic measurement data manager that records, in the measurement table, the measurement data inputted by the measurement data inputter so as to create an association with the image of the measurement object every time an optical characteristic of the measurement object is measured, the measurement data manager recording, in the measurement table, the measurement data concerning the measurement object corresponding to the image inputted by the image inputter when the normal mode is set, the measurement data manager recording, in the measurement table, the measurement data concerning the measurement object corresponding to the image selected by the image selector when the image specification mode is set.

6. The electronic support apparatus as claimed in claim 5, further comprising:
- an electronic display on a display surface of which the image selected by said image selector is displayed.

7. The electronic support apparatus as claimed in claim 6, wherein an image input screen to prompt input of the image of the measurement object is displayed on the display surface of the display before the input of the measurement data by the measurement data inputter when the normal mode is set.

8. The electronic support apparatus as claimed in claim 5, further comprising:
- an electronic part specifier configured to specify a measurement part of the measurement object;
- wherein said measurement data manager assigns a measurement part number to the part specified by said part specifier, and records the inputted measurement data in the measurement table so as to create an association with the measurement part number.

9. The electronic support apparatus as claimed in claim 5, further comprising:
- an electronic number of times specifier configured to specify the number of times the measurement is performed on the same part of the measurement object;
- wherein said measurement data manager assigns a measurement data number to the measurement data of each time of the specified number of times of measurement, and records the inputted measurement data in the measurement table so as to create an association with the measurement data number.

10. The electronic support apparatus as claimed in claim 5, further comprising:
- an electronic object discrimination information inputter configured to input object discrimination information to discriminate the measurement object;
- wherein said measurement data manager records the inputted measurement data in the measurement table so as to create an association with the object discrimination information.

11. A computer program product stored on a tangible computer readable medium containing instructions executable by a computer in a support apparatus for optical characteristic measurement, said instructions stored on said computer program product being configured, when executed by the computer, to make the computer perform a process comprising the steps of:
- inputting an image of a measurement object;
- registering the inputted image of the measurement object;
- inputting a measurement data of the measurement object obtained by an optical characteristic measuring instrument;
- generating a measurement table to record the measurement data and the image of the measurement object corresponding to the measurement data;
- selecting the image corresponding to one measurement object from registered images;
- setting a normal mode or an image specification mode;
- recording, in the measurement table, the measurement data concerning the measurement object corresponding to the inputted image when the normal mode is set; and
- recording, in the measurement table, the measurement data concerning the measurement object corresponding to the image selected by the image selector when the image specification mode is set.

12. The program product as claimed in claim 11, wherein said computer program product includes instructions that, when executed by the computer, make the computer perform the step of displaying the selected image.

13. The program product as claimed in claim 11, wherein said computer program product includes instructions that, when executed by the computer, make the computer perform the step of displaying an image input screen to prompt input of the image of the measurement object before the input of the measurement data when the normal mode is set.

14. The program product as claimed in claim 11, wherein said computer program product includes instructions that, when executed by the computer, make the computer perform the steps of:
- specifying a measurement part of the measurement object;
- assigning a measurement part number to the specified part; and
- recording the inputted measurement data in the measurement table so as to create an association with the measurement part number.

15. The program product as claimed in claim 11, wherein said program product includes instructions that, when executed by the computer, make the computer perform the steps of:
- specifying the number of times the measurement is performed on the same part of the measurement object;
- assigning a measurement data number to the measurement data of each time of the specified number of times of measurement; and
- recording the inputted measurement data in the measurement table so as to create an association with the measurement data number.

16. The program product as claimed in claim 11, wherein said program product includes instructions that, when executed by the computer, make the computer perform the steps of:
- inputting object discrimination information to discriminate the measurement object; and recording the inputted measurement data in the measurement table so as to create an association with the object discrimination information.

17. A computer-based support apparatus for optical characteristic measurement comprising:
- a CPU;
- memory;
- a data storage device;
- an input circuit for receiving optical characteristic measurement data obtained by an optical characteristic measuring instrument; and
- an input circuit for receiving an image of a measurement object;
- wherein the apparatus is programmed to:
- register an received image of the measurement object;
- select an image corresponding to one measurement object from registered images;
- set a normal mode or an image specification mode; and
- when a normal mode is set, record, in a measurement table, received measurement data concerning the measurement object corresponding to the received image so as to create an association with said received measurement data with the received image of the measurement object when an optical characteristic of the measurement object is measured, and
- when a image specification mode is set, record, in a measurement table, received measurement data concerning the measurement object corresponding to the selected image so as to create an association with said received measurement data with the selected image of a measurement object when an optical characteristic of the measurement object is measured.

18. A computer-based support apparatus for optical characteristic measurement comprising:
- a CPU;
- memory;
- a data storage device;
- an input circuit for receiving an image of a measurement object and for receiving optical characteristic measurement data, separate from the image of the object, obtained by an optical characteristic measuring instrument;
- wherein the apparatus is programmed to:
- update a measurement table in which the optical characteristic measurement data and the image of the measurement object corresponding to the measurement data are recorded; and
- record the optical characteristic measurement data, received by the input circuit, in the measurement table so as to create an association with the measurement data with the image of the measurement object each time an optical characteristic of the measurement object is measured.

* * * * *

UNITED STATES PATENT AND TRADEMARK OFFICE
CERTIFICATE OF CORRECTION

| | |
|---|---|
| PATENT NO. | : 7,668,408 B2 |
| APPLICATION NO. | : 11/398792 |
| DATED | : February 23, 2010 |
| INVENTOR(S) | : Kimura et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Seventh Day of December, 2010

David J. Kappos
*Director of the United States Patent and Trademark Office*